(12) United States Patent
Khairkhahan et al.

(10) Patent No.: US 12,150,644 B2
(45) Date of Patent: Nov. 26, 2024

(54) SUTURE CLIP AND SUTURE CLIP APPLIER

(71) Applicant: Vquad Medical LLC, Palo Alto, CA (US)

(72) Inventors: Sebastian Khairkhahan, Palo Alto, CA (US); Alexander Khairkhahan, Palo Alto, CA (US)

(73) Assignee: VQuad Medical, LLC, Palo Alto, CA (US)

( * ) Notice: Subject to any disclaimer, the term of this patent is extended or adjusted under 35 U.S.C. 154(b) by 206 days.

(21) Appl. No.: 17/740,002

(22) Filed: May 9, 2022

(65) Prior Publication Data

US 2022/0257238 A1    Aug. 18, 2022

Related U.S. Application Data

(62) Division of application No. 16/241,855, filed on Jan. 7, 2019, now Pat. No. 11,324,496.

(Continued)

(51) Int. Cl.
*A61B 17/04* (2006.01)
*A61B 17/00* (2006.01)

(52) U.S. Cl.
CPC ...... *A61B 17/0487* (2013.01); *A61B 17/0469* (2013.01); *A61B 2017/00946* (2013.01); *A61B 2017/0488* (2013.01)

(58) Field of Classification Search
CPC ... A61B 17/128; A61B 17/1285; A61B 17/08; A61B 17/10; A61B 17/105;

(Continued)

(56) References Cited

U.S. PATENT DOCUMENTS

| 2,256,382 | A | * | 9/1941 | Dole | A61B 17/0682 72/409.05 |
| 4,291,698 | A | | 9/1981 | Fuchs et al. | |

(Continued)

FOREIGN PATENT DOCUMENTS

| CN | 104394783 A | * | 3/2015 | ......... A61B 17/0682 |
| WO | WO-2019160799 A1 | | 8/2019 | |

OTHER PUBLICATIONS

EP19755021.3 Extended Search Report dated Jan. 7, 2022.

(Continued)

*Primary Examiner* — Katherine M Shi
(74) *Attorney, Agent, or Firm* — Wilson Sonsini Goodrich & Rosati

(57) ABSTRACT

A suture clip includes a disc body having at least two adjacent portions joined by a hinge at one end and a latch at another end. Suture engagement surfaces are formed on a first and second portion of the disc body so that the first and second suture engagement surfaces can close sufficiently tightly to immobilize a pair of suture lengths therebetween when the two portions are closed and held together by the latch. A suture clip applier holds a plurality of such suture clips typically in a magazine, an open configuration where the suture engagement surfaces are held apart. Single suture clips are advanced by an advancement mechanism over a pair of suture ends having a midsection in tissue. A closing mechanism closes and latches the first and second portions of the disc body together to capture the pair of suture ends therebetween.

11 Claims, 8 Drawing Sheets

Related U.S. Application Data

(60) Provisional application No. 62/631,355, filed on Feb. 15, 2018.

(58) Field of Classification Search
CPC .......... A61B 17/068; A61B 2017/0688; A61B 17/0487; A61B 2017/0404; A61B 2017/0454; A61B 2017/0488; A61B 2017/0438; A61B 17/0401
See application file for complete search history.

(56) References Cited

U.S. PATENT DOCUMENTS

| | | | |
|---|---|---|---|
| 5,160,339 A | 11/1992 | Chen et al. | |
| 5,234,449 A | 8/1993 | Bruker et al. | |
| 5,330,442 A | 7/1994 | Green et al. | |
| 9,498,202 B2 | 11/2016 | Jafari et al. | |
| 11,324,496 B2 | 5/2022 | Khairkhahan et al. | |
| 2003/0233142 A1 | 12/2003 | Morales et al. | |
| 2010/0125297 A1 | 5/2010 | Guederian et al. | |
| 2010/0256676 A1 | 10/2010 | Hay et al. | |
| 2012/0290005 A1 | 11/2012 | Martin et al. | |
| 2013/0158600 A1 | 6/2013 | Conklin et al. | |
| 2013/0226237 A1 | 8/2013 | Stanley et al. | |
| 2014/0018829 A1 | 1/2014 | Patani | |
| 2014/0277124 A1 | 9/2014 | Rosenthal et al. | |
| 2016/0213371 A1 | 7/2016 | Miraki et al. | |
| 2016/0270776 A1 | 9/2016 | Miraki et al. | |
| 2017/0119374 A1 | 5/2017 | Gaerke et al. | |

OTHER PUBLICATIONS

Final Office action dated Feb. 5, 2021 for U.S. Appl. No. 16/241,855.
International Search Report and Written Opinion for PCT/US2019/017465 on Jun. 25, 2019.
Office action dated Oct. 1, 2021 for U.S. Appl. No. 16/241,855.
Office action dated Oct. 19, 2020 for U.S. Appl. No. 16/241,855.
U.S. Appl. No. 16/241,855 Notice of Allowance dated Apr. 7, 2022.
U.S. Appl. No. 16/241,855 Notice of Allowance dated Jan. 21, 2022.

* cited by examiner

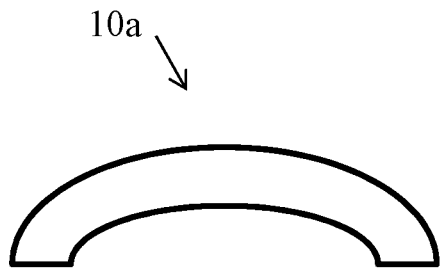
FIG. 3A
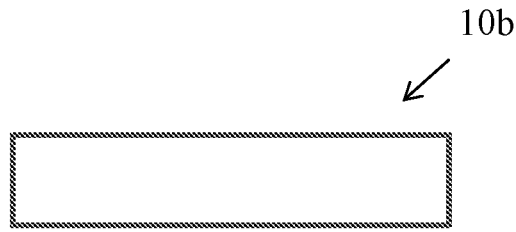
FIG. 3B
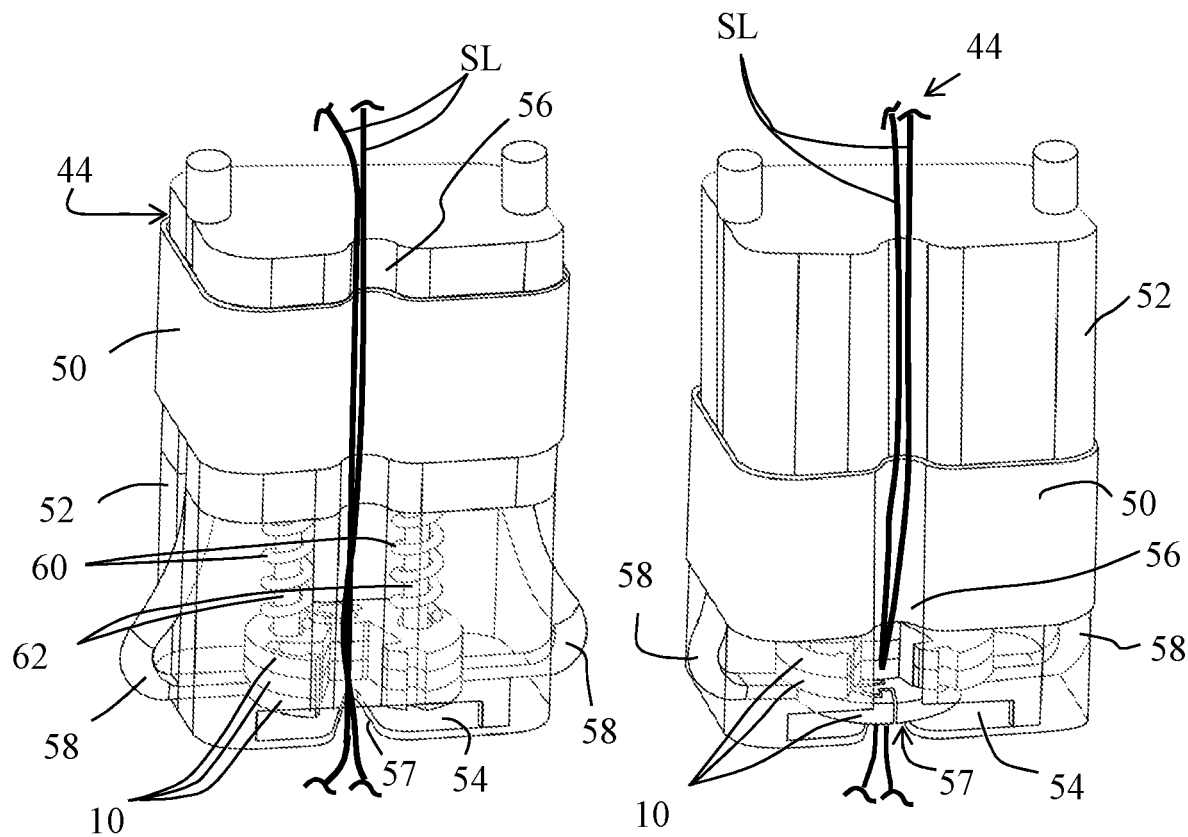
FIG. 5A
FIG. 5B

SUTURE CLIP AND SUTURE CLIP APPLIER

CROSS-REFERENCE TO RELATED APPLICATION

This application is a divisional of U.S. patent application Ser. No. 16/241,855, filed Jan. 7, 2019, now U.S. Pat. No. 11,324,496, granted on May 10, 2022, which claims the benefit of provisional application 62/631,355, filed on Feb. 15, 2018, the full disclosure of which is incorporated herein by reference.

BACKGROUND OF THE INVENTION

1. Field of the Invention. The present invention relates generally to medical devices and methods. More specifically, the present invention relates to devices and methods for clipping free suture ends in open and minimally invasive surgical procedures.

The use of sutures for closing incisions and securing implanted devices is ubiquitous in both open and minimally invasive surgical procedures. Commonly, the free ends of a length of suture are knotted to close an incision or secure an implanted device to tissue. Knotting surgical suture can be a difficult skill for some surgeons to master and, even for the most skilled, can be tedious and time consuming. The tension left in the sutures can be difficult to control, the knots can be difficult or impossible to untie, and knots can accidentally come loose. Thus, a number of clips and other suture securement devices have been proposed as improvements to manual knotting, and many of these alternative devices are now in common use.

While often a significant improvement over conventional knotting, many suture clips and clip appliers are limited in their ability to rapidly deploy multiple clips onto a series of the sutures which have been placed in conjunction with, e.g., performing an anastomosis, securing an annuloplasty ring of prosthetic heart valve, closing a lengthy incision, or the like.

It is therefore an object of the present invention to provide improved suture securement clips and apparatus and methods for their deployment. In particular, it is an object of the present invention to provide suture securement clips and clip appliers which permit rapid, sequential closure of multiple suture lengths that have been pre-positioned in tissue, e.g. for performing an anastomosis, securing an annuloplasty ring or prosthetic heart valve, closing a lengthy incision, or the like. At least some of these objectives will be met by the inventions described herein.

2. Description of the Background Art. Suture clips and other securement devices are described in U.S. Pat. Nos. 9,498,202; 5,330,442; 5,160,339; and 4,291,698, and U.S. Pat. Publ. Nos. US2017/119374 and US2016/270776. US2016/213371 describes a suture clip applier.

SUMMARY OF THE INVENTION

The present invention provides devices, systems, and methods for closing sutures which have been pre-placed in tissue for any of a variety of purposes, such as closing incisions, attaching implants, and the like. The present invention is particularly useful for the sequential delivery of multiple suture clips for securing pairs of free suture ends over tissue in a rapid and reliable manner.

In a first aspect, the present invention provides a suture clip comprising a body typically formed as a circular or other shaped disk having two adjacent portions joined by a hinge at a first location on a perimeter of the disk body. The adjacent portions are typically formed as halves of the disk body, e.g., having half-moon shapes, and the disk body typically has a latch mechanism at a second location on the perimeter diametrically opposed to the first location when the disk body is circular. Suture engagement surfaces are formed on each of the first portion and the second portion of the disk body such that the engagement surfaces close sufficiently tightly to immobilize a pair of suture lengths therebetween when the two portions are closed and held together by the latch.

In specific aspects, the hinge of the suture clip is a living hinge formed in a metal or polymeric disk body material. In other specific instances, the latch of the suture clip comprises a barb on the first portion of the disk body and a locking arm on the second portion of the disk body. In still further specific embodiments, the disk body further includes a barrier formed above the hinge to center the suture between the engagement surfaces on the two portions of the disk body as the portions are closed and latched. More specifically, the barrier may comprise a rest arm projecting from below the suture engagement surface on one of the adjacent portions of the disk body and a slot formed in the suture engagement surface on the other of the adjacent portions of the disk body. In this way, the arm acts as a backstop for the suture when the suture is captured in the suture clip prior to closure of the disk body portion. As the disk body portions close, the barrier is received in the slot in the opposed disk body portion.

In still other specific instances, the two adjacent portions in the disk body are divided along a diametric line so that each portion has an area approximately close to one-half (½) of the disk body area, typically having an area in the range from about 45% to 55% of the total disk body area. In still further specific instances, the two adjacent portions of the disk body are held apart by the hinge in an open configuration in order to receive suture prior to closing the portions that capture the suture there between. In such instances, the latch will hold the disk body closed in order to secure the suture. The hinge can be elastic or malleable and either open or closed when free from external forces. For example, the disk body will typically be open when free from constant and have a malleable hinge that can be closed by an external clamping force. Alternatively, the disk body may be closed when free from constraint with an elastic hinge that allows the disk body to be held open by an associated clip applier when positioning the clip over suture. The two portions of the disk body will self-close over the suture when released from constraint. Even in such self-closing embodiments, however, the latch will typically be closed by an external clamp to assure that the clip tightly holds the suture over time.

In some specific embodiments of the present invention, the disk body can be generally planar while in other specific embodiments the disk body may have an arcuate cross-section in order to conform to a curved surface, e.g. a curved surface of the body, of an an implant, or the like.

In a second specific aspect of the present invention, a suture clip applier comprises a shaft having a proximal end and distal end. A magazine housing is secured to the distal end of the shaft and has a dispensing slot in the wall thereof. A stack of suture clips is disposed within the magazine housing, where the individual clips are held in an open configuration with spaced-apart suture engagement surfaces. The suture clip applier further includes a mechanism for advancing a distal-most of the open suture clips to a position within the housing adjacent to the dispensing slot. A compression mechanism is disposed to laterally compress and close the distal-most clip while that clip remains present in the housing to secure sutures between the suture engagement surfaces of the clip. After the suture engagement surfaces of the suture clip have been secured over the sutures, the compressed clips may be released through though the dispensing slot in the housing. It is an advantage of this design that the clips remain contained within the housing at all times until they are engaged onto the suture so that they cannot be accidently released.

In specific aspects, the suture clips delivered by the clip applier each comprise a disk body (generally as described previously) having two adjacent portions joined by hinge at the first location on the perimeter of the disk body and having a latch at a second location on the perimeter diametrically opposed to the first location. Suture engagement surfaces on each of the portions are disposed so that they would tightly immobilize a pair of suture length there between when closed by the compression mechanism.

In other specific embodiments, each disk body will have at least one guide hole, and typically two guide holes formed therein. The clip applier will include guide rails in the housing to retain the stack of clips and prevent premature release. Typically, only the distal-most clip will be released from the guide rails after that clip has been advanced to its position adjacent to the dispensing slot. The distal-most clip will be held in place by the compression mechanism while in an open position adjacent to the dispensing slot. Only after the compression of mechanisms closes the clip, and the compression mechanism is opened, will the distal-most clip be released and be free to exit through the dispensing slot. Typically, the compression mechanism comprises a pair of opposed closing arms present in or immediately outside of the housing. The closing arms can be actuated, pulled, or otherwise deployed by a sliding sleeve or other mechanism which forces the closing arms to move inwardly toward each other to compress the distal-most clip while it is held therebetween. After closure, the closing arms may be opened to release the disk body which has been immobilized over the tissue closure or other target site.

In a third specific aspect of the present invention, a suture clip comprises a disc body having two adjacent portions joined by a hinge at a first location on a perimeter of the disc body and a barrier above the hinge to center a length of suture between the two portions of the disc body. Suture engagement surfaces are formed on first and second portions of the disc body, and the first and second suture engagement surfaces close sufficiently tightly to immobilize a pair of suture lengths therebetween when the two portions are closed together. Such suture clips comprising the suture barrier may optionally also include a latch and other any or all features of the present invention as described elsewhere herein.

BRIEF DESCRIPTION OF THE DRAWINGS

FIG. 3A is a side view of the suture clip of FIG. 1, showing the suture clip having an arcuate profile.

FIG. 3B is a side view of the clip of FIG. 1, showing an embodiment having a planar profile.

FIGS. 5A and 5B are detailed views of a clip magazine of the type used in the clip delivery tool of FIG. 4.

DETAILED DESCRIPTION OF THE INVENTION

Figure 1:
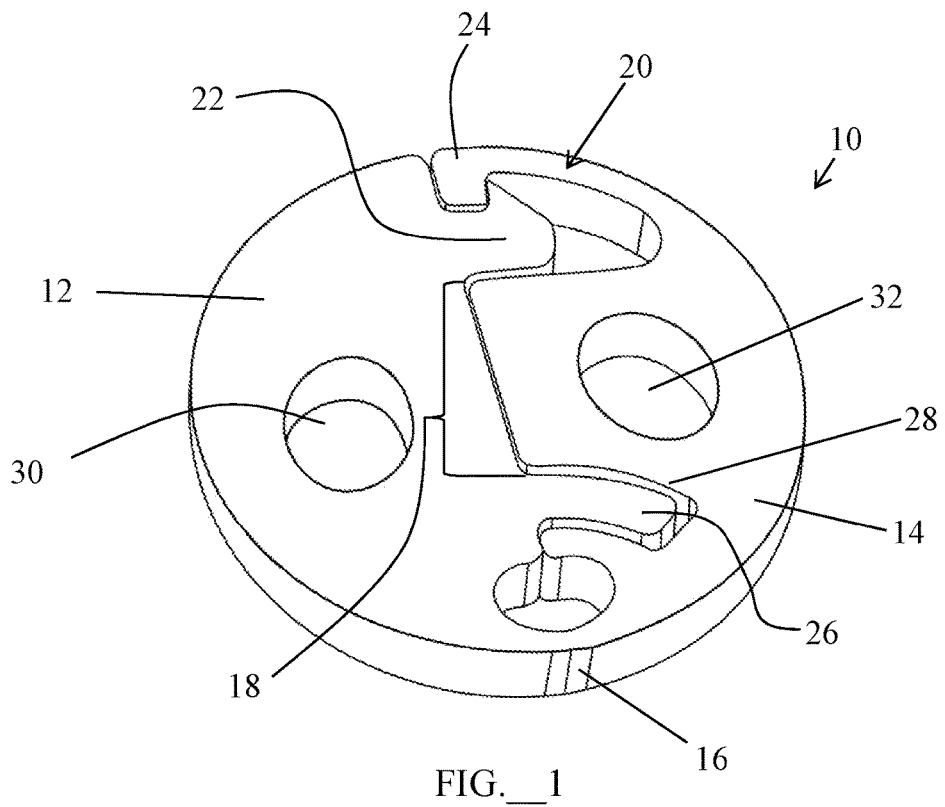
FIG. 1 is a perspective view of a suture clip constructed in accordance with the principles of the present invention.
Figure 2A:
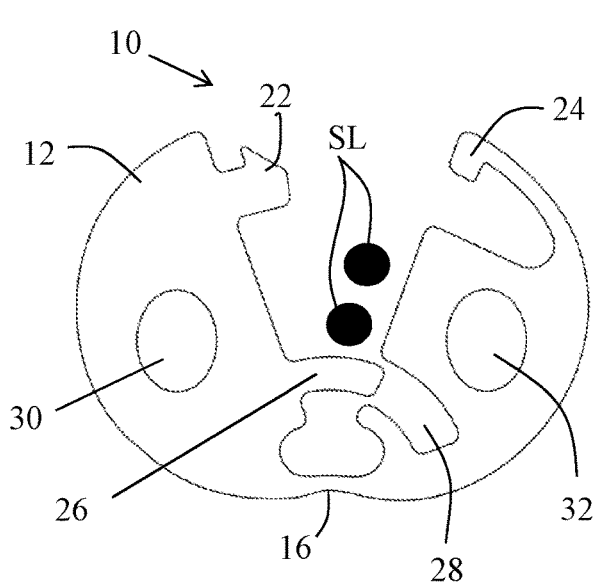
FIG. 2A is a top view of the suture clip of FIG. 1 shown in an open position with a pair of suture lengths held between engagement surfaces of the clip.
Figure 2B:
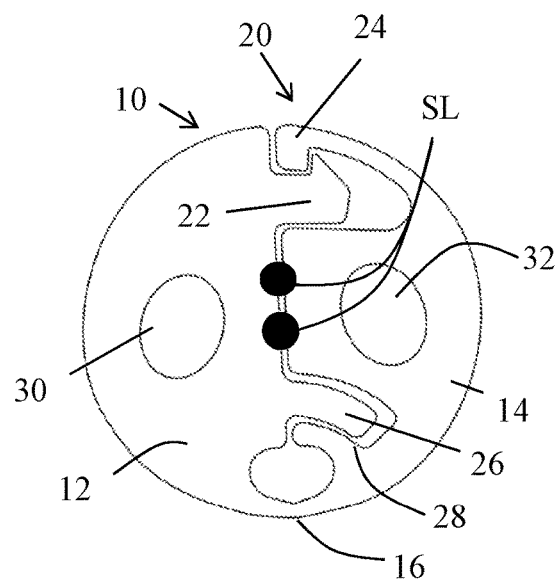
FIG. 2B is a view of the suture clip of FIG. 2A after the opposed portions of the suture clip have been closed to secure the suture lengths therebetween.

Referring to FIG. 1, a suture clip 10 includes a first portion or half 12 joined to a second portion or half 14 by a hinge 16. The suture clip 10 is shown in a closed configuration in FIG. 1 but can assume an opened configuration, as shown in FIG. 2A, as well as a closed configuration with suture lengths SL, as shown in FIG. 2B. The hinge 16 is typically a living hinge, i.e., one that is formed by the material of the disk body of the suture clip and which elastically or inelastically deforms between the opened and closed configurations of the suture clip.

The suture lengths SL are held in a locking zone 18 formed by opposed surfaces on each of the first and second portions 12 and 14, respectively, of the disk body of the suture clip 10. A latch mechanism 20 is provided in order to assure a tight closure of the two portions of the disk body and typically includes a barb 22 formed on one of the portions and a locking arm 24 formed on the other of the portions. In this way, the two portions can be closed from the configuration shown in FIG. 2A so that the barb 22 engages the locking arm 24 with the engagement surfaces in the locking zone 18 tightly closed against one another in order to secure the suture lengths SL therebetween.

The suture clip 10 typically also includes a resting arm 26 which projects outwardly from the first portion 12 of the suture clip at a location just above the hinge 16. The resting arm 26 is received in a slot 28 formed in the second portion 14 of the suture clip so that the two portions can be closed. The resting arm 26 acts as a "back stop" to maintain the suture lengths SL within the locking zone 18 and prevent the suture lengths from accidently entering an open gap which forms part of the hinge structure 16. In addition to the features described thus far, the suture clips will typically also include first and second guide holes 30 and 32 which are used to stack multiple suture clips 10 in a clip delivery tool 40 (FIG. 4), as will be described hereinafter.

The disk body of the suture clip 10 may have either an arcuate profile, as shown at 10a in FIG. 3A, or a planar profile 10b, as shown in FIG. 3B. The planar profile will be suitable for most purposes. An arcuate profile will be useful when the clip is used on a curved tissue surfaces, implant surfaces, or other situations where a curved clip profile will conform to an adjacent surface.

Figure 4:
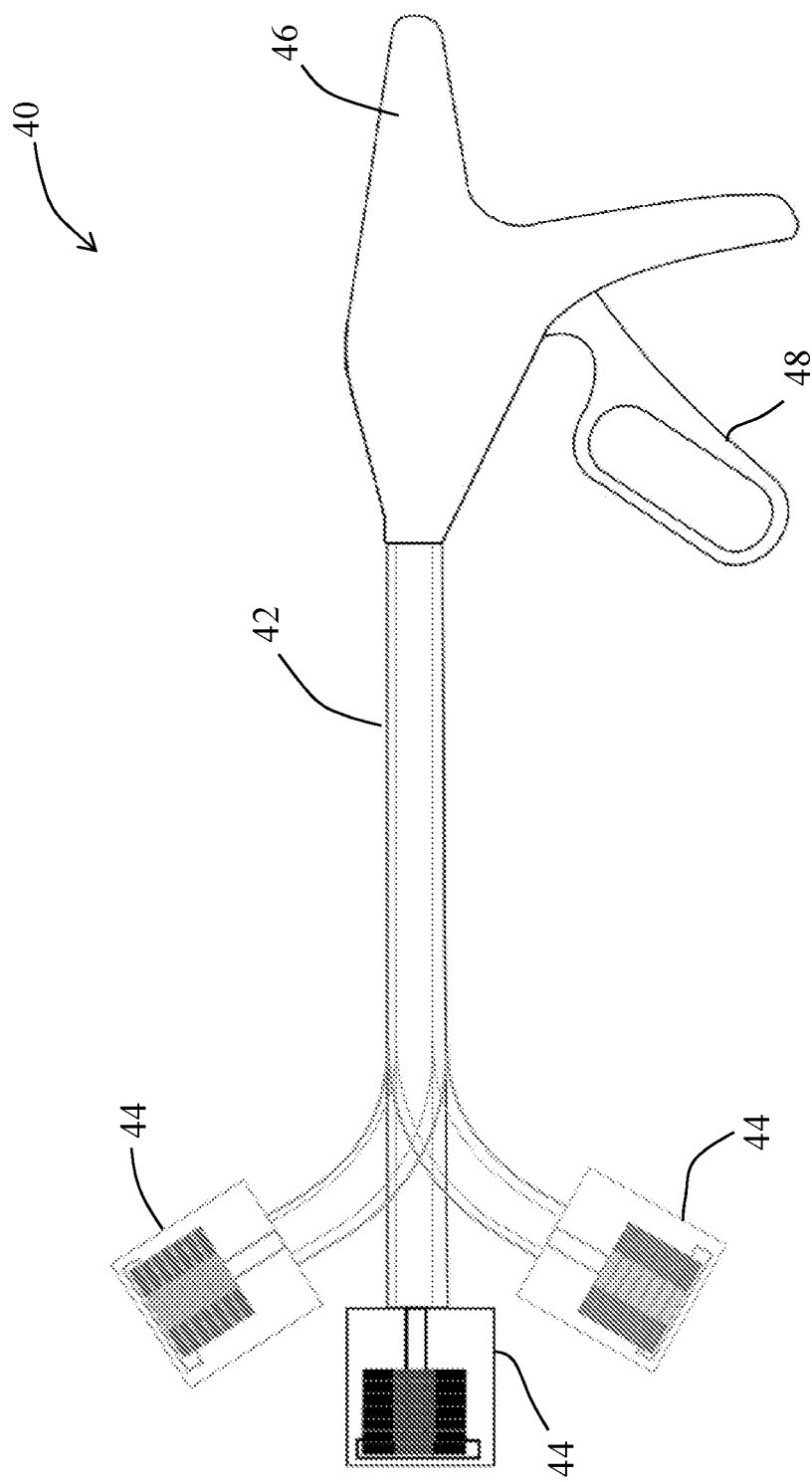
FIG. 4 is a side view of a clip delivery tool constructed in accordance with the principles of the present invention showing deflected distal end configurations in phantom view.

Referring now to FIG. 4, a clip delivery tool 40 constructed in accordance with principles of the present invention comprises a shaft 42 having a magazine 44 at a distal end thereof and a handle 46 at a proximal end thereof. The handle includes a trigger 48 which is used to delivery individual suture clips 10 from the magazine 44, as will be described below. Optionally, the shaft may have a flexible or deformable distal end (shown in phantom view) so the magazine can be repositioned for better access to remote tissue sites.

Referring to FIGS. 5A and 5B, the suture clip magazine 44 comprises a housing 52 having a dispensing slot 54 formed at a distal-most end thereof. A suture-receiving channel or groove 56 is formed along one surface of the housing so that suture may be received therein and passed through a V-shaped notch 57 at the bottom of the housing. A pair of closure or crimping arms 58 is disposed on opposed lateral sides of the housing 52 and have distal clip-engaging ends which are aligned with the dispensing slot 54 in the housing. A plurality of suture clips 10 are stacked on guideposts 62 within the housing 52 and are urged in a distal direction by a pair of advancement springs 60. In this way, a distal-most of the suture clips 10 (at the bottom in FIGS. 5A and 5B) will be maintained adjacent the dispensing slot 54 and between the distal ends of the crimping arms 58.

As shown in FIG. 5A, the distal-most suture clip 10 remains in its open configuration (FIG. 2A) with suture length SL present in the suture channel 56 and passing through the open suture clip and the V-shaped notch 57. Once the suture lengths are thus positioned in the opening of the suture clip 10 between the engagement surfaces of the locking zone 18, the handle 48 on the clip delivery tool 40 can be actuated to advance a slider 50, as shown in FIG. 5B, in order to compress and close the crimping arms 58 in order to fully close the distal-most suture clip 10, as shown in FIG. 5B. At that point, the trigger can be released, allowing the slider 50 to move proximally and release the crimping arm 58 from the distal-most suture clip 10. At that point, the closed suture clip (FIG. 2B) can be pulled away, leaving the suture clip in place over the tissue, as shown in FIGS. 7A and 7B below.

Figure 6A:
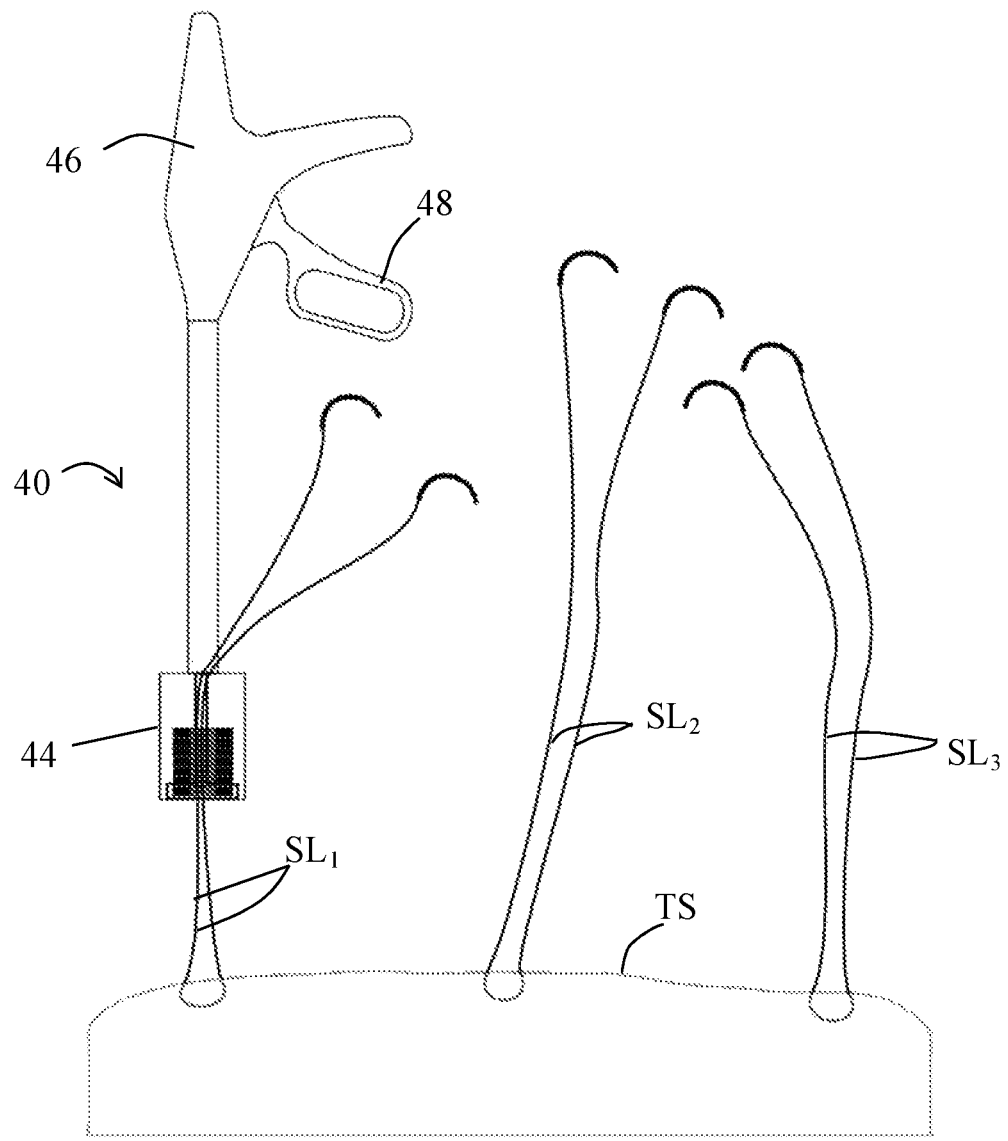
FIG. 6A through 6D illustrate use of the clip delivery tool of FIG. 4 for sequentially delivering a plurality of suture clips to a plurality of suture length.
Figure 6B:
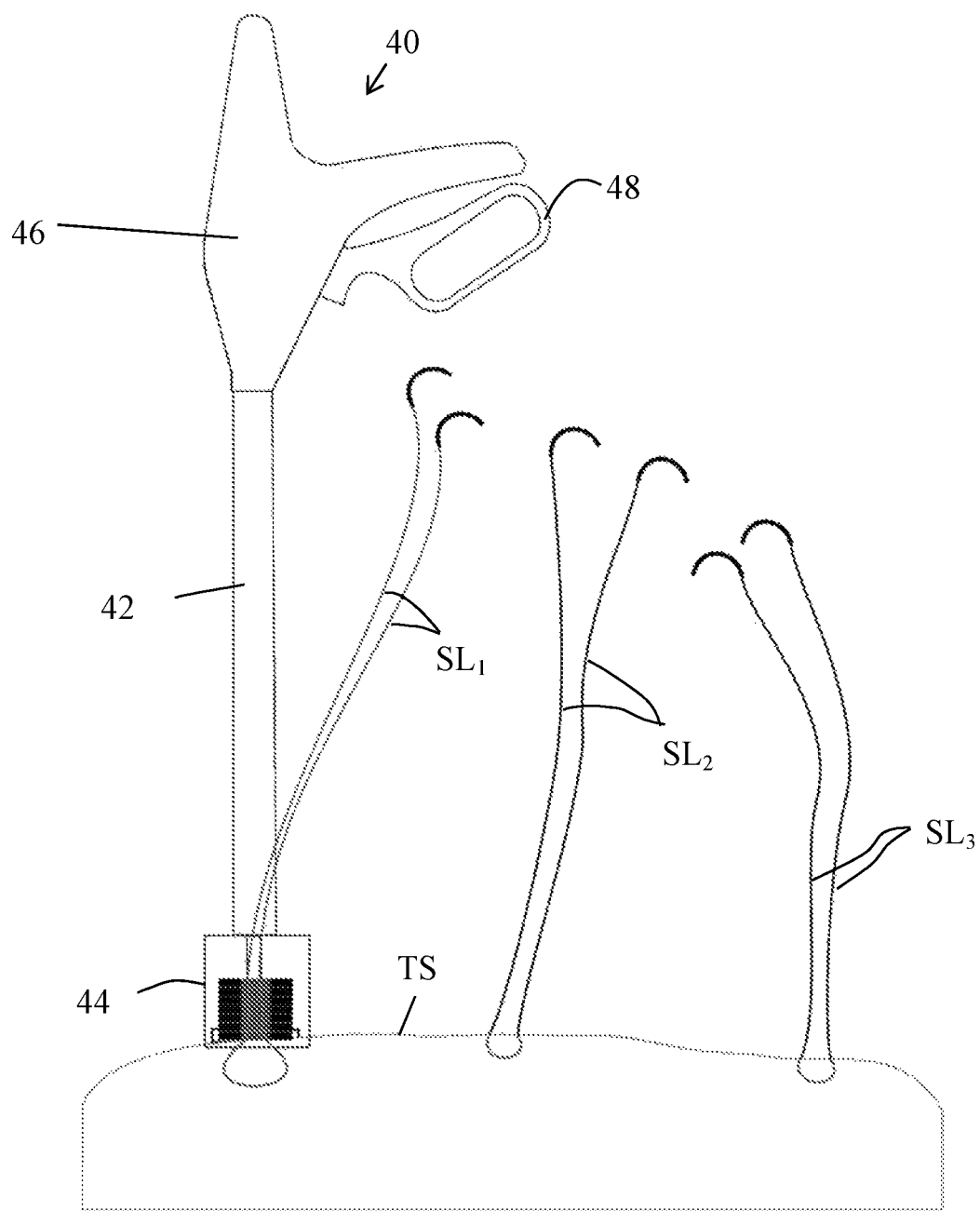
Figure 6C:
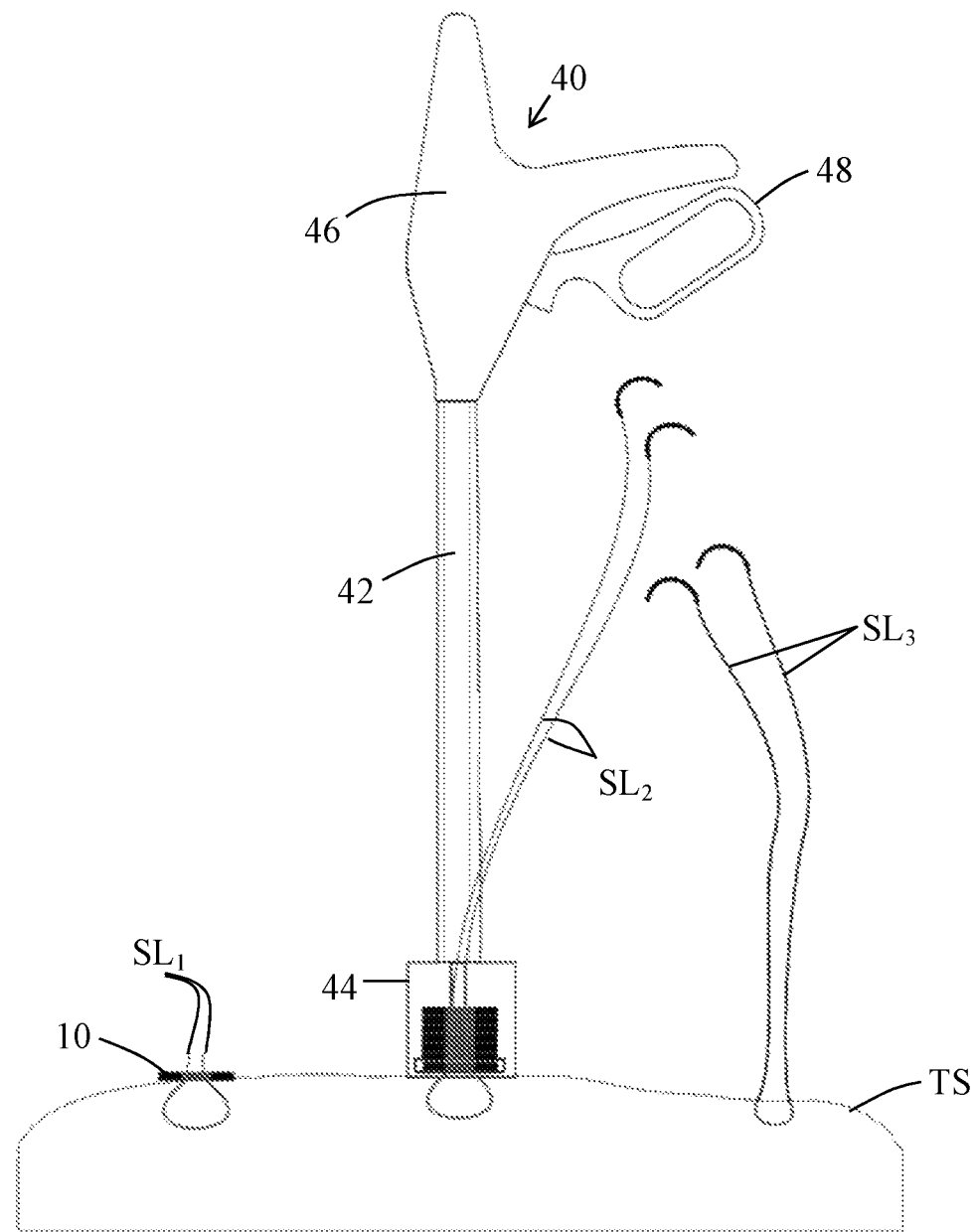
Figure 6D:
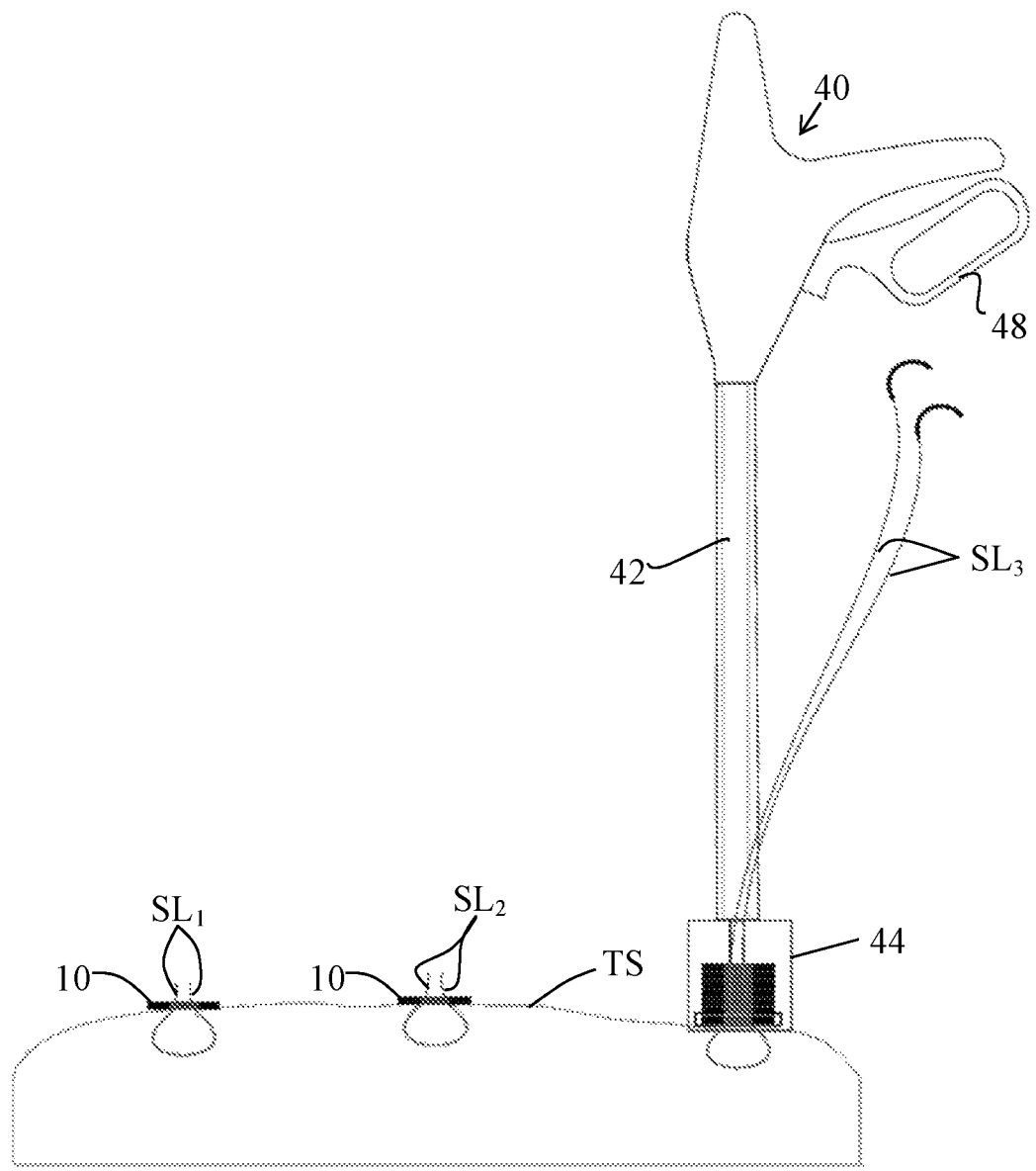

Use of the clip delivery tool 40 for sequentially delivering multiple suture clips 10 is described with reference to FIG. 6A through 6D. As shown in FIG. 6A, the magazine 44 is initially engaged to capture adjacent strands of a first suture length $SL_1$ to c in the suture channel 56 of the magazine. As the magazine 44 is pressed down against the tissue surface TS, the user will also pull upwardly on the first suture $SL_1$ to tension the suture prior to suture clip closure, as shown in FIG. 6B. The trigger 48 on handle 46 has then actuated in order to close the suture clip, and the clip applier 40 pulled away. The excess suture can then be trimmed, and the magazine moved to a second suture length $SL_2$, as shown in FIG. 6C. The clip delivery tool 40 is then actuated to then deliver a second clip 10 over the second suture length $SL_2$, and the second suture length then trimmed. The clip delivery tool 40 can then be moved to a third suture length $SL_3$, and the procedure repeated in order to place a third suture clip 10 on the third suture length.

Figure 7A:
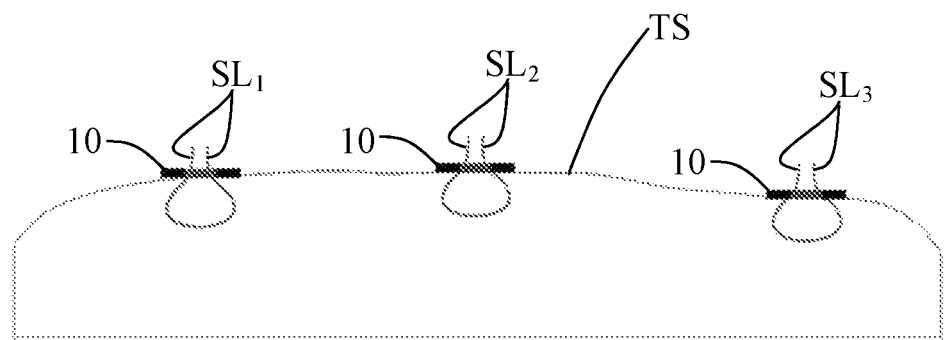
FIGS. 7A and 7B are side and top views, respectively, of the multiple suture clips after delivery as illustrated in FIG. 6A through 6D.
Figure 7B:
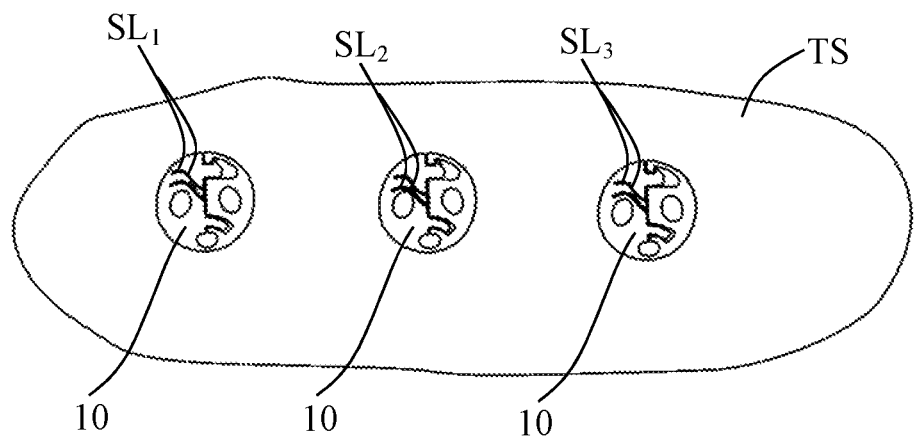

After the procedure is complete, three suture clips 10 will be placed on the first through third suture length as shown in FIGS. 7A and 7B. FIG. 7A shows a side view of the suture clips while FIG. 7B shows a top view of the suture clips.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A suture clip applier comprising:
    a shaft having a proximal end and a distal end;
    a magazine housing secured to the distal end of the shaft, said magazine housing having a dispensing slot;
    a stack of suture clips disposed in the magazine housing, wherein the suture clips are held in an open configuration with spaced-apart suture engagement surfaces;
    a mechanism for advancing a distal-most of the open suture clips to a position within the housing adjacent to the dispensing slot;
    a mechanism for compressing the distal-most clip in the housing to secure sutures between the suture engagement surfaces;
    wherein the compressed clip is configured to be released and passed passes through the slot after being compressed over a suture;
    wherein each suture clip of the stack of suture clips comprises:
        a disc body having two adjacent portions joined by a hinge at a first location on a perimeter of the disc body and having a latch at a second location on the perimeter of the disc body diametrically opposite to the first location,
        wherein a first suture engagement surface of the spaced-apart suture engagement surfaces is disposed on a first portion of the disc body and a second suture engagement surface of the spaced-apart suture engagement surfaces is disposed on a second portion of the disc body, and
        wherein the first and second suture engagement surfaces are configured to close sufficiently tightly to immobilize a pair of suture lengths therebetween when the two portions are closed and held together by the latch.

2. A suture clip applier as in claim 1, wherein each portion of the two adjacent portions has a guide hole formed therein and where the guide holes are received over guide rails in the magazine housing of the suture clip applier.

3. A suture clip applier as in claim 2, wherein the guide rails terminate at locations in the magazine housing such that the distal-most suture clip is released from the guide rails so that it can be released through the dispensing slot after closure.

4. A suture clip applier as in claim 2, wherein the guide rails retain the stack of suture clips to prevent premature release.

5. A suture clip applier as in claim 1, wherein the mechanism for advancing a distal-most of the open suture clips to a position within the housing adjacent to the dispensing slot comprises a spring configured to advance the stack of suture clips each time the distal-most suture clip is released through the dispensing slot.

6. A suture clip applier as in claim 1, wherein the mechanism for compressing the distal-most clip in the housing to secure sutures between the suture engagement surfaces comprises a pair of opposed closing arms disposed in the housing adjacent to the dispensing slot.

7. A suture clip applier as in claim 6, wherein the pair of opposed closing arms can be actuated, pulled, or otherwise deployed by a sliding sleeve to force each of the closing arms to move inwardly toward each other, thereby compressing the distal-most clip while it is held therebetween.

8. A suture clip applier as in claim 1, wherein the distal-most clip is configured to be contained within the magazine housing at least until the distal-most clip is engaged onto the secured sutures.

9. A suture clip applier as in claim 1, wherein the hinge is a living hinge.

10. A suture clip applier as in claim 1, wherein the hinge is malleable so that it is configured to be closed by the application of an external closing force.

11. A suture clip applier as in claim 1, wherein the latch comprises a barb on the first portion of the disc body and a locking arm on the second portion of the disc body.

* * * * *